United States Patent
Ohly et al.

(10) Patent No.: US 7,943,025 B2
(45) Date of Patent: May 17, 2011

(54) SENSOR ELEMENT FOR DETERMINING A PHYSICAL PROPERTY OF A MEASURING GAS

(75) Inventors: Christian Ohly, Weil der Stadt (DE); Walter Strassner, Schorndorf (DE); Joachim Graeber, Heilbronn (DE); Ulrich Eisele, Stuttgart (DE); Lothar Diehl, Gerlingen (DE); Thomas Seiler, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 368 days.

(21) Appl. No.: 12/129,761

(22) Filed: May 30, 2008

(65) Prior Publication Data
US 2008/0296156 A1    Dec. 4, 2008

(30) Foreign Application Priority Data
May 31, 2007   (DE) .................. 10 2007 025 234

(51) Int. Cl.
G01N 27/417    (2006.01)

(52) U.S. Cl. ..... 204/429; 204/424; 204/428; 205/783.5; 205/784; 73/23.31; 73/23.32

(58) Field of Classification Search .......... 204/424–429; 205/783.5–785, 781; 73/23.31–23.32
See application file for complete search history.

(56) References Cited

U.S. PATENT DOCUMENTS

| 4,857,165 | A * | 8/1989 | Ishiguro et al. | 204/424 |
| 2003/0205078 | A1 * | 11/2003 | Hasei et al. | 73/23.31 |
| 2004/0007462 | A1 * | 1/2004 | Hotta et al. | 204/429 |

FOREIGN PATENT DOCUMENTS

DE    10305856    9/2004

* cited by examiner

Primary Examiner — Nam X Nguyen
Assistant Examiner — Bach T Dinh
(74) Attorney, Agent, or Firm — Kenyon & Kenyon LLP

(57) ABSTRACT

A sensor element is provided for determining a physical property of a measuring gas, especially of the concentration of at least one gas component in the measuring gas, which has at least one ceramic layer, a diffusion barrier adjoining the at least one ceramic layer and at least one electrode that is exposed to the measuring gas diffusing through the diffusion barrier. In order to reduce the production variations with respect to the static pressure dependence and the limiting current of the diffusion barrier), the proportions of silicon in the diffusion barrier and in the at least one ceramic layer are approximately equal and differ by not more than 1 wt. %.

9 Claims, 1 Drawing Sheet

SENSOR ELEMENT FOR DETERMINING A PHYSICAL PROPERTY OF A MEASURING GAS

CROSS-REFERENCE

This application claims benefit under 35 U.S.C. §119 of German Patent Application DE 102007025234.1, filed on May 31, 2007, which is expressly incorporated herein by reference in its entirety.

FIELD OF THE INVENTION

The present invention relates to a sensor element for determining a physical characteristic of a measuring gas, in particular the concentration of a gas component in the measuring gas.

BACKGROUND INFORMATION

A conventional sensor element for a broadband lambda probe for determining the oxygen concentration in the exhaust gas of an internal combustion engine, described in, for example, German Patent No. DE 103 05 856 A1, has a stratified structure of ceramic layers that are made up of a solid electrolyte, such as zirconium oxide ($ZrO_2$) having proportions of silicon oxide ($SiO_2$) and yttrium oxide ($Y_2O_3$). Between two solid electrolyte layers a gas chamber is formed, which is covered by a diffusion barrier from a gas access opening, that is inserted into the one solid electrolyte layer. A measuring electrode, or Nernst electrode, and an inner pump electrode are situated in the gas chamber. The inner pump electrode, which is situated on one solid electrolyte layer, together with an outer pump electrode that is situated on the outer side of the same solid electrolyte layer, and is exposed to the exhaust gas, forms a so-called pump cell, by which oxygen is pumped in and out of the gas chamber. The measuring electrode or Nernst electrode situated on the other solid electrolyte layer forms a measuring cell, or Nernst cell, together with a reference electrode that is exposed to a reference gas. One additional solid electrolyte layer, which is laminated together with the two other solid electrolyte layers, bears on its side lying against the one solid electrolyte layer an electrical heating element that is embedded in an insulating layer made of aluminum oxide ($Al_2O_3$). The sensor element thus constructed is subsequently exposed to a sintering process.

In order to produce the diffusion barrier, a paste is used that is composed generally of $ZrO_2$ having proportions of $SiO_2$ and $Y_2O_3$, and is packed with a pore-forming material. During the sintering of the sensor element, the pore-forming material evaporates or burns, and leaves pores in the material through which the exhaust gases are able to diffuse and get into the gas chamber, during operation of the sensor element. In the process, the silicon proportion of the paste accelerates its sintering, while the yttrium proportion lowers the sintering activity. The silicon proportion in the paste is less and the yttrium proportion greater, compared to the adjoining solid electrolyte layers. Because of the sintering activity in the paste that is diminished thereby, a size reduction or a closing of the pores, left behind by the pore-forming material after it is burned out, is damped. During the sintering of the sensor element, the greater silicon proportion of the solid electrolyte layer also influences the sintering activity in the paste of the diffusion barrier. In the border areas of the diffusion barrier that adjoin the solid electrolyte layers, there will be greater sintering, in this context, than in the middle areas, which will result in smaller pores in the border area. Whereas in thick diffusion barriers the percentage proportion of more greatly sintered border areas is low at the entire diffusion barrier, the more greatly sintered border areas, in the case of thin diffusion barriers, have a nonnegligible effect on the static pressure dependence of the diffusion barrier, because the smaller pores, whose diameter is smaller than the free path of the gas molecules, increase the proportion of Knudsen diffusion, and thus the proportion of the static pressure dependence of the oxygen transport by the solid electrolyte. This leads to an uncontrolled variation in the useful signal of the sensor element.

SUMMARY

An example sensor element according to the present invention may have the advantage that, because of the provision of approximately equal silicon proportions in the diffusion barrier and in the ceramic layer adjoining it, the sintering behavior of the ceramic layer and the diffusion barrier is largely the same, and the silicon proportions of the ceramic layer have no significant effect on the sintering properties of the diffusion barrier in its border area. That being the case, the sintering properties of the diffusion barrier are largely independent of the thickness of the diffusion barrier. The thickness of the diffusion barrier, which determines the size of the limiting current of the sensor element, may thus be set as desired, without having intolerable manufacturing variations of the static pressure dependence and the limiting current taking place because of the sintering, by requiring the reworking of the diffusion barrier, for instance, by lasering after the sintering of the sensor element, or other adjustment measures in the plug connector of the sensor element.

BRIEF DESCRIPTION OF THE DRAWINGS

The present invention is explained in greater detail below on the basis of exemplary embodiments illustrated in the figures.

DETAILED DESCRIPTION OF EXAMPLE EMBODIMENTS

Figure 1:
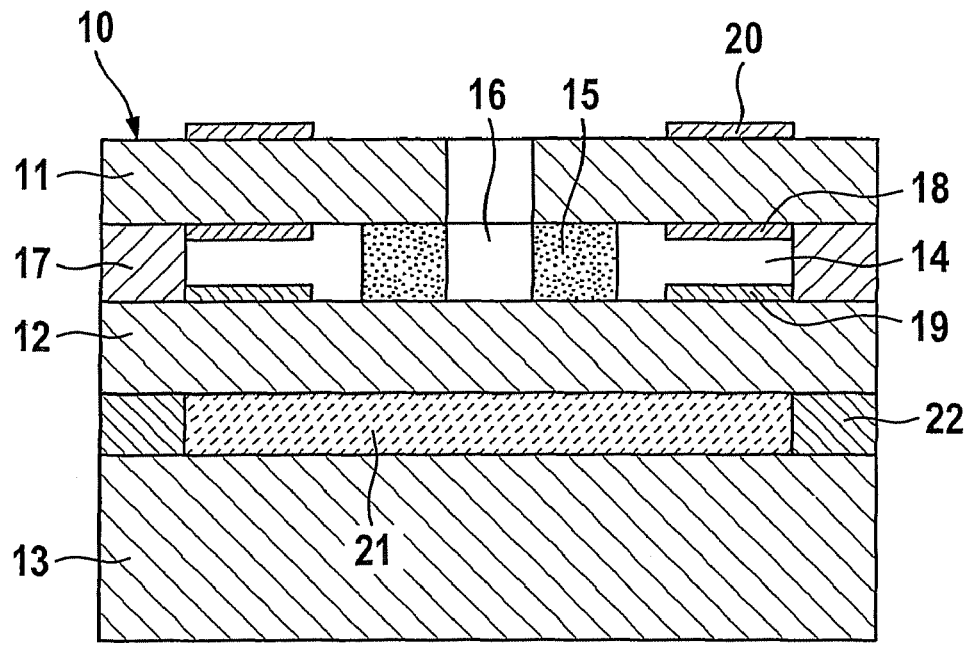
FIG. 1 shows a cross section of an example sensor element for a broadband lambda probe.

The sensor element, shown schematically in cross section in FIG. 1, has a planar sensor body 10 which is composed of several ceramic layers. It has a first, second and third solid electrolyte layer 11, 12, 13 of zirconium oxide ($ZrO_2$) having an yttrium oxide ($Y_2O_3$) component and a silicon oxide ($SiO_2$) component. At least solid electrolyte layers 11, 12, are each made up, for instance, of 90 wt. % $Y_2O_3$ and 1.1 wt. % $SiO_2$. Between first and second solid electrolyte layer 11, 12, there is situated an annular measuring gas chamber 14, in whose middle region there is an annular, porous diffusion barrier 15. The measuring gas located outside sensor body 10 is able to reach measuring gas chamber 14 via a gas access opening 16, that is inserted into first solid electrolyte layer 11, and which opens out into the middle of diffusion barrier 15 and via diffusion barrier 15. Measuring gas chamber 14 is sealed laterally by a sealing frame 17. On the inside of measuring gas chamber 14, at first solid electrolyte layer 11, an inner pump electrode 18 is situated, and at second solid electrolyte layer 12 a measuring electrode or Nernst electrode 19 is situated. On the outside of first solid electrolyte layer 11 that is exposed to the measuring gas, an outer pump electrode 20 is situated which, together with inner pump electrode 18, forms a so-called pump cell. Nernst electrode 19, together with a reference electrode, not shown here, which is exposed to a reference gas, e.g., environmental air, forms a so-called Nernst cell. The Nernst cell measures the partial pressure of the oxygen in measuring gas chamber 14. The pump cell pumps oxygen in such a way into measuring gas chamber 14 or out of measuring gas chamber 14 that there is a partial oxygen pressure of λ=1 in measuring gas chamber 14. The current flowing over the pump cell is a measure for the concentration of oxygen in the measuring gas.

A heating element 21 is provided between the second and the third solid electrolyte layer 12, 13, which includes a heating circuit trace which is separated by an insulation from the surrounding solid electrolyte layers. Heating element 21 is surrounded laterally by a heater frame 22, which electrically insulates heater element 21 and seals it in a gas-tight manner.

Diffusion barrier 15 is produced from a paste which is made up of zirconium oxide ($ZrO_2$) having $SiO_2$ and $Y_2O_3$ proportions. A pore-forming material, for example made of vitreous carbon or theobromine, is admixed to the paste, and it burns or evaporates in response to the sintering of the sensor element, and leaves pores in diffusion barrier 15 at the end of the sintering process. The proportions of $SiO_2$ and $Y_2O_3$ influence the sintering process and also the closing of the pores left behind after the burning out of the pore-forming material. During sintering, $SiO_2$ leads to a liquid grain boundary phase which accelerates the sintering. $Y_2O_3$ reduces the sintering activity. In a later sintering stage, $SiO_2$ reacts partially with $ZrO_2$ to form $ZrSiO_4$. However, this reaction first requires the formation of $ZrSiO_4$ nuclei, and therefore only occurs delayed toward the end of the sintering process.

During sintering, the silicon proportions of solid electrolyte layers 11 and 12 also influence the sintering activity in diffusion barrier 15. In the border regions of diffusion barrier 15 towards solid electrolyte layers 11, 12, a strongly sintered region is created having increasing sintering of the pores created by the burning out of the pore-forming material. The pores, that are smaller because of that, increase the proportion of Knudsen diffusion in diffusion barrier 15, and thus the static pressure dependence of the diffusion barrier. Whereas, in the case of a thick diffusion barrier 15, the volume proportion of the more strongly sintered boundary regions is relatively small as a ratio to the overall volume of diffusion barrier 15, and leads to possibly acceptable production variations in the static pressure dependence, in the case of a thin diffusion barrier 15, the percentage proportion of the regions of diffusion barrier 15 that is more strongly sintered because of the influence of solid electrolyte layers 11, 12 is considerable, and production variations in the static pressure dependence are created which require reworking the sensor element after sintering, for instance, by partial removal of diffusion barrier 15 using a laser.

In order to suppress such uncontrolled production variations and to make the sintering property of diffusion barrier 15 independent of the thickness of diffusion barrier 15, the silicon proportion and the yttrium proportion in diffusion barrier 15 are adapted to the silicon proportion and the yttrium proportion in solid electrolyte layer 11, 12, that is, they are made approximately of the same size. The silicon proportions of diffusion barrier 15 and solid electrolyte layers 11 and 12 differ, in this context, by not more than 1 wt. %, while the yttrium proportions in diffusion barrier 15 and solid electrolyte layers 11 and 12 differ by not more than 3 wt. %. As was described at the outset, in the case of a combined solid electrolyte layer 11, 12, the components of diffusion barrier 15 amount, for example, to 94 wt. % $ZrO_2$, 5.4 wt. % $Y_2O_3$ and 0.33 wt. % $SiO_2$. In the example shown, solid electrolyte layers 11, 12 have the greater Si proportion and the greater yttrium proportion. However, the difference in the proportions is smaller than was mentioned above.

Figure 2:
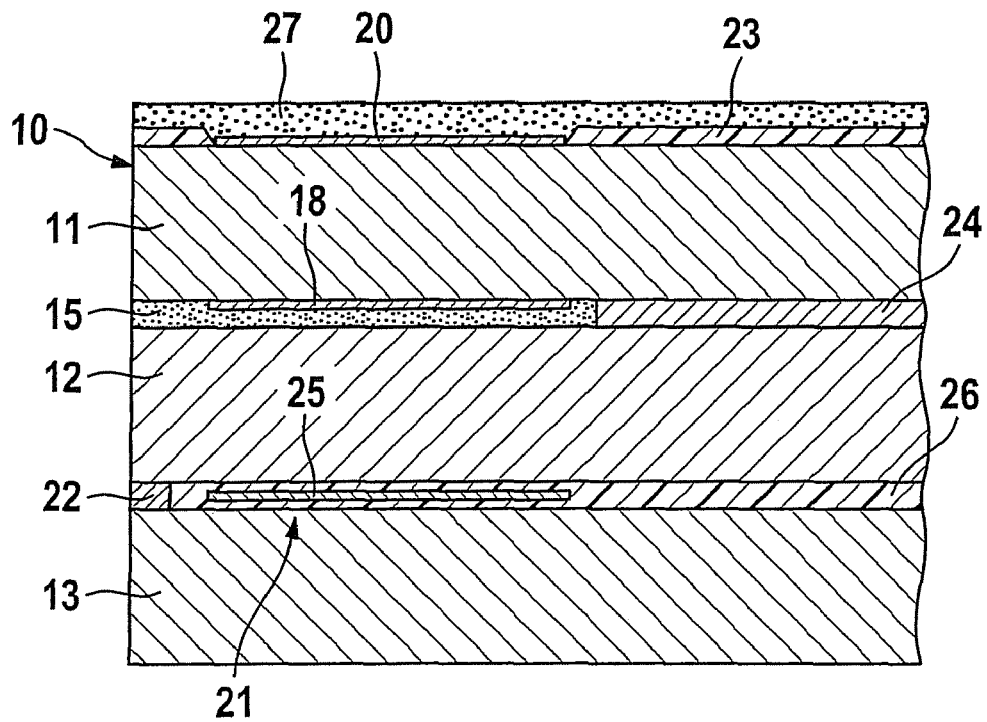
FIG. 2 shows, in a cutout, a longitudinal section of a sensor element for a lean probe or a limiting current probe.

The sensor element shown as a cutout in longitudinal section in FIG. 2, for a lean probe or a limiting current probe, is made in turn of a planar element of three solid electrolyte layers 11, 12 and 13, laminated together by sintering, and having the same composition as given above. The outer side of first solid electrolyte layer 11, facing the measuring gas, is covered using an insulating layer 23, and, in a recess of insulating layer 23, outer pump electrode 20 is in turn situated on solid electrolyte layer 11. On the other, inner side of solid electrolyte layer 11, opposite outer pump electrode 20, inner pump electrode 18 is situated. A thin, porous diffusion barrier 15 is laid over inner pump electrode 18, and it reaches all the way to the end face of sensor body 10, and is thus exposed with its end face to the measuring gas that surrounds sensor body 10. Thin diffusion barrier 15 is composed of the same components at the same proportions as was described above for FIG. 1. An adjustment layer 24 covers the remaining area of solid electrolyte layer 11. Between second solid electrolyte layer 12 and third solid electrolyte layer 13, in turn, heating element 21 is situated, which includes a heating circuit trace 25 that is separated from the surrounding solid electrolyte layers 12, 13 by an insulation 26. Insulation 26 is enclosed by heating frame 22 that is impermeable to gas Outer pump electrode 20 as well as insulating layer 23 are coated over their entire surface with a protective layer 27.

What is claimed is:

1. A sensor element for determining a physical property of a concentration of at least one gas component in a measuring gas, comprising:
   at least one ceramic layer including a base material having a silicon component and a yttrium component;
   a diffusion barrier adjoining the at least one ceramic layer, the diffusion barrier including a base material having a silicon component and a yttrium component; and
   at least one electrode adapted to be exposed to the measuring gas diffusing through the diffusion barrier;
   wherein a proportion of the silicon in the diffusion barrier and in the at least one ceramic layer are approximately equal and do not differ by more than 1 wt.%.

2. The sensor element as recited in claim 1, wherein the proportions of yttrium in the at least one ceramic layer and in the diffusion barrier are approximately equal and do not differ by more than 3 wt.%.

3. The sensor element as recited in claim 1, wherein the at least one ceramic layer has a greater silicon proportion than the diffusion barrier.

4. The sensor element as recited in claim 2, wherein the at least one ceramic layer has a greater yttrium proportion than the diffusion barrier.

5. The sensor element as recited in claim 1, wherein the ceramic layer and the diffusion barrier have zirconium oxide as the base material.

6. The sensor element as recited claim 1, wherein the diffusion barrier is situated between two of the ceramic layers.

7. The sensor element as recited in claim 6, wherein the at least one electrode is situated between the diffusion barrier and one of the two ceramic layers.

8. The sensor element as recited in claim 6, wherein a measuring gas chamber that accommodates the at least one electrode is situated between the two ceramic layers, and the diffusion barrier is situated between a gas access and the measuring gas chamber.

9. The sensor element as recited in claim 8, wherein the gas access is a gas access opening in at least one of the two ceramic layers.

* * * * *